United States Patent [19]

Chandraratna et al.

[11] Patent Number: 5,498,755
[45] Date of Patent: Mar. 12, 1996

[54] DISUBSTITUTED ARYL AND HETEROARYL IMINES HAVING RETINOID-LIKE BIOLOGICAL ACTIVITY

[76] Inventors: Roshantha A. Chandraratna, 25841 Empresa, Mission Viejo, Calif. 92691; Min Teng, 133 Southbrook, Irvine, Calif. 92714

[21] Appl. No.: 294,901

[22] Filed: Aug. 23, 1994

[51] Int. Cl.$^6$ ................................ C07C 251/24
[52] U.S. Cl. ............ 564/272; 560/35; 562/440; 564/172; 564/270; 564/274
[58] Field of Search .............. 560/35; 562/440, 562/624; 564/270, 272, 172, 274

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 542/429 |
| 4,391,731 | 7/1983 | Boller et al. | 252/299.62 |
| 4,695,649 | 9/1987 | Magami et al. | 560/86 |
| 4,723,028 | 2/1988 | Shudo | 560/8 |
| 4,739,098 | 4/1988 | Chandraratna | 560/8 |
| 4,740,519 | 4/1988 | Shroot et al. | 514/443 |
| 4,810,804 | 3/1989 | Chandraratna | 514/311 |
| 4,826,969 | 5/1989 | Maignan et al. | 536/55.2 |
| 4,826,984 | 5/1989 | Berlin et al. | 546/134 |
| 4,855,320 | 8/1989 | Chatterjee et al. | 514/473 |
| 4,895,868 | 1/1990 | Chandraratna | 514/432 |
| 4,927,947 | 5/1990 | Chandraratna | 549/484 |
| 4,980,369 | 12/1990 | Chandraratna | 514/432 |
| 4,992,468 | 2/1991 | Chandraratna | 514/532 |

(List continued on next page.)

FOREIGN PATENT DOCUMENTS

| | | | |
|---|---|---|---|
| 0098591 | 1/1984 | European Pat. Off. | C07D 333/54 |
| 0130795 | 1/1985 | European Pat. Off. | C07D 311/58 |
| 170105A | 7/1985 | European Pat. Off. | |
| 0176033 | 4/1986 | European Pat. Off. | C07D 261/18 |
| 0176032 | 4/1986 | European Pat. Off. | C07C 65/38 |
| 176034A | 4/1986 | European Pat. Off. | C07C 63/66 |
| 0253302 | 1/1988 | European Pat. Off. | C07D 213/16 |
| 0272921 | 6/1988 | European Pat. Off. | C07D 213/80 |
| 0284288 | 9/1988 | European Pat. Off. | C07D 401/04 |
| 0303915 | 2/1989 | European Pat. Off. | A61K 31/255 |
| 0315071 | 5/1989 | European Pat. Off. | C07C 63/66 |
| 0350846 | 7/1989 | European Pat. Off. | C07D 311/58 |
| 3316932 | 11/1983 | Germany | C07C 63/66 |
| 3524199 | 1/1986 | Germany | C07C 63/66 |
| 3602473 | 7/1987 | Germany | C07C 43/215 |
| 3708060 | 9/1987 | Germany | C07D 311/04 |
| 3715955 | 11/1987 | Germany | C07C 15/58 |
| 2190378 | 11/1987 | United Kingdom | C07C 39/21 |
| 8500806 | 2/1985 | WIPO | A61K 31/00 |
| 8504652 | 10/1985 | WIPO | A61K 31/19 |
| WO9116051 | 10/1991 | WIPO | A61L 31/44 |
| 9117139 | 11/1991 | WIPO | |
| WO9206948 | 4/1992 | WIPO | C07C 69/86 |

OTHER PUBLICATIONS

Baudin, CA 116:235267, 1991.
A General Synthesis of Terminal and Internal Arylalkynes by the Palladium–Catalyzed Reaction of Alkynylzinc Reagents with Aryl Halides by Anthony O. King and Ei–ichi Negishi, *J. Org. Chem.* 43 No. 2, 1978 p. 358.
Conversion of Methyl Ketones into Terminal Acetylenes and (E)–Tri–substituted Olefins of Terpenoid Origin by Ei–ichi, Anthony O. King and William L. Klima, *J. Org. Chem.* 45 No. 12, 1980 p. 2526.
Sporn et al. in *J. Amer. Acad. Derm.* 15:756–764 (1986).
A Convenient Synthesis of Ethynylarenes and Diethynylarenes by S. Takahashi, Y. Kuroyama, K. Sonogashira, N. Hagihara, *Synthesis* 1980 pp. 627–630.
Shudo et al. in *Chem. Phar. Bull.* 33:404–407 (1985).
Kagechika et al. in *J. Med. Chem.* 31:2182–2192 (1988).
Chemistry and Biology of Synthetic Retinoids by Marcia I. Dawson and William H. Okamura, published by CRC Press Inc., 1990, pp. 334–335, 354.
Synthesis of 2,2'–Diacyl–1,1'–biaryls. Regiocontrolled Protection of . . . by Mervic, et al, *J. Org. Chem.*, No. 45, pp. 4720–4725, 1980.
A Dopamine Receptor Model and Its Application in the Design of a New Class of Rigid Pyrrolo[2,3–g]isoquinoline Antipsychotics, Gary L. Olson, et al. *American Chemical Society,* 1981, Vo. 24, No. 9, pp. 1026–1031.
6.2.3 Conformational Restriction, Williams, et al., *Drug Discovery and Development,* 1987 The Humana Press, pp. 54–55.

(List continued on next page.)

*Primary Examiner*—Yogendra N. Gupta
*Attorney, Agent, or Firm*—Gabor L. Szekeres; Robert J. Baran; Martin A. Voet

[57] ABSTRACT

Compounds of the formula

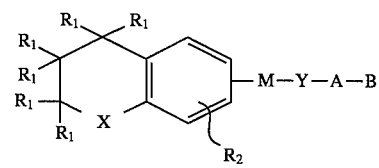

wherein the $R_1$ groups independently are hydrogen, lower alkyl, or two geminal $R_1$ groups jointly represent an oxo (=O) or a thio (=S) group; $R_2$ is hydrogen or lower alkyl, or halogen; M is or $-N=CR_4-$ or $-R_4C=N-$ where $R_4$ is hydrogen or lower alkyl; X is $C(R_1)_2$; Y is phenyl optionally substituted with an $R_3$ group which is lower alkyl or halogen; A is $(CH_2)_n$ where n is 0–5, lower branched chain alkyl, cycloalkyl, alkenyl, alkynyl; B is hydrogen, COOH or a pharmaceutically acceptable salt thereof, $COOR_8$, $CONR_9R_{10}$, $-CH_2OH$, $CH_{2OR_{11}}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons have retinoid-like biological activity.

7 Claims, No Drawings

U.S. PATENT DOCUMENTS

| | | | |
|---|---|---|---|
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1993 | Chandraratna | 564/163 |

OTHER PUBLICATIONS

Davis et al. *J. Organomettalic Chem* 387 (1990) 381–390.

Effects of 13–Cis–Retinoic Acid, All–Trans–Retinoic Acid, and Acitretin on the Proliferation, Lipid Synthesis and Keratin Expression of Cultured Human Sebocytes In Vitro, C. C. Zouboulis, *The Journal of Investigative Dermatology*, vol. 96, No. 5, May 1991, pp. 792–797.

Organ maintenance of human sebaceous glands: in vitro effects of 13–cis retinoic acid and testosterone, John Ridden, et al., Journal of Cell *Science*, Vo. 95, 1990, pp. 125–136.

Characterization of Human Sebaceous Cells In Vitro, Thomas I. Doran, et al., *The Journal of Investigative Dermatology*, vol. 96, No. 3, Mar. 1991.

Synthesis and Evaluation of Stilbene and Dihydrostilbene Derivatives as Potential Anticancer Agents That Inhibit Tubulin Polymerization by Cushman, Mark et al. *J.Med. Chem* 1991, 34, 2579–2588.

Synthesis and Evaluation of New Protein–Tyrosine Kinase Inhibitors. Part 1. Pyridine–Containing Stilbenes and Amides by Cushman, Mark et al. *Bioorganic & Medicinal Chemistry Letters*, vol. 1, No. 4, pp. 211–214, 1991.

Di–and Tri–methoxystyryl Derivatives of Heterocyclic Nitrogen Compounds by Bahner, C. T. et al. Arzneim–Forsch.Drug Res. 31 (I), Nr. 3 (1981).

Retinobenzoic acids. 3. Structure–Activity Relationships of retinoidal Azobenzene–4–carboxylic acids and Stilbene–4–carboxylic acids by H. Kagechika et al., *Journal of Medicinal Chemistry*, 1989, 32, pp. 1098–1108.

DISUBSTITUTED ARYL AND HETEROARYL IMINES HAVING RETINOID-LIKE BIOLOGICAL ACTIVITY

FIELD OF THE INVENTION

The present invention relates to novel compounds having retinoid-like activity. More specifically, the present invention relates to compounds having an imine function which is substituted on the one hand with a 5,6,7,8-tetrahydronaphthyl, chromanyl, thiochromanyl or 1,2,3,4-tetrahydroquinolinyl group and by a substituted aryl or substituted heteroaryl group having a carboxylic acid ester or carboxylic acid function. The acid function may also be converted to an alcohol, aldehyde or ketone or derivatives thereof, or may be reduced to —CH$_3$.

BACKGROUND ART

Compounds which have retinoid like activity are well known in the art, and are described in numerous United States and foreign patents and in scientific publications. It is generally known and accepted in the art that retinoid like activity is useful for treating animals of the mammalian species, including humans, for curing or alleviating the symptoms and conditions of numerous diseases and conditions. In other words, it is generally accepted in the art that pharmaceutical compositions having a retinoid like compound or compounds as the active ingredient are useful as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus) for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

U.S. Pat. Nos. 4,980,369, 5,089,509, 5,162,546, and 5,175,185 disclose acetylene compounds which are substituted by a chromanyl, thiochromanyl or tetrahydroquinolinyl group and by a substituted phenyl or heteroaryl group, having retinoid-like biological activity.

U.S. Pat. Nos. 5,013,744, 5,175,185 and 5,264,456 disclose acetylene compounds which are substituted by an alkylphenyl, alkoxyphenyl or thioalkoxyphenyl group and by a heteroaryl carboxylic acid or carboxylic acid ester group, having retinoid-like biological activity.

U.S. Pat. No. 4,992,468 discloses diphenyl ethylene compounds having retinoid like biological activity. EPO patent application No. 0130795 discloses chroman or thiochroman and phenyl substituted ethylene compounds having retinoid-like biological activity.

U.S. Pat. Nos. 5,006,550, 5,015,658, 5,130,335, 5,143, 159, and 5,231,113 disclose esters and thioesters of substituted phenol compounds (such as of para-hydroxy benzoic acid) with 5,6,7,8-tetrahydronaphthoic acid, chromanoic acid or thiochromanoic acid, having retinoid like biological activity.

U.S. Pat. No. 5,037,825 discloses compounds having retinoid-like biological activity where a condensed heterocyclic ring such as a thiochroman is connected to a substituted phenyl ring with an ethylene, or amide (CONH) bridge. An article in Journal of American Academy of Dermatology by Sporn et. al. and an article in Journal of Medicinal Chemistry, 1988, 31, 2182–2193 (Kagechika et al.) also disclose compounds of retinoid-like biological activity where a tetrahydronaphthalene, chroman or thiochroman moiety and a benzoic acid moiety are connected by an amide (CONH) bridge.

Several co-pending applications and recently issued patents assigned to the assignee of the present application, are directed to further compounds having retinoid-like activity.

SUMMARY OF THE INVENTION

The present invention covers compounds of Formula 1

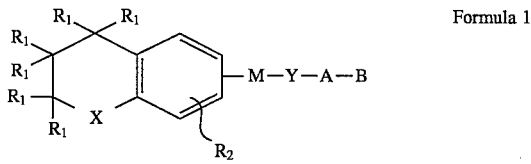

Formula 1 wherein the R$_1$ groups independently are hydrogen, lower alkyl of 1 to 6 carbons, or two geminal R$_1$ groups may represent an oxo (=O) or a thio (=S) group;

R$_2$ is hydrogen or lower alkyl of 1 to 6 carbons, or halogen;

M is —N=CR$_4$— or —R$_4$C=N— where R$_4$ is hydrogen or lower alkyl of 1–6 carbons;

X is C(R$_1$)$_2$, O, S, or NR$_1$;

Y is a phenyl group, or heteroaryl selected from a group consisting of pyridyl, thienyl, furyl, pyridazinyl, pirimidinyl, pyrazinyl, thiazolyl, imidazolyl and oxazolyl, said phenyl group or said heteroaryl groups being optionally substituted with an R$_3$ group which is lower alkyl of 1 to 6 carbons or halogen;

A is (CH$_2$)$_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, or CR$_7$OR$_{13}$O, where R$_7$ is an alkyl, cycloalkyl or alkenyl group containing 1 to 5 carbons, R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons.

In a second aspect, this invention relates to the use of the compounds of Formula 1 as regulators for cell proliferation and differentiation, and particularly as agents for treating dermatoses, such as acne, Darier's disease, psoriasis, icthyosis, eczema, atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus), for treating chronic inflammatory diseases such as pulmonary fibrosis, for treating and preventing diseases associated with lipid metabolism and transport such as dyslipidemias, for promoting wound healing, for treating dry eye syndrome and in reversing and preventing the effects of sun damage to skin.

This invention also relates to a pharmaceutical formulation comprising a compound of Formula 1 in admixture with a pharmaceutically acceptable excipient.

In another aspect, this invention relates to the process for making the "imine" compound of Formula 1 which process comprises reacting in an inert solvent a primary amine of Formula 2 with an aldehyde or ketone of Formula 3, or to reacting an aldehyde or ketone of Formula 4 with a primary amine of Formula 5. In Formulas 3 and 5, B' is defined as B above, or such a protected derivative of the B function which does not interfere with the formation of the imine function in the indicated reactions. The remaining symbols are defined as in connection with Formula 1.

General Embodiments

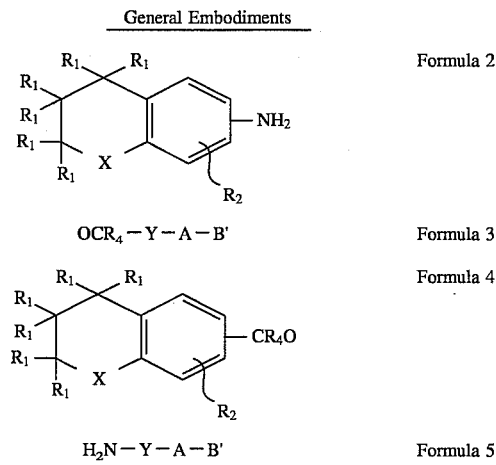

Formula 2

OCR$_4$—Y—A—B'  Formula 3

Formula 4

H$_2$N—Y—A—B'  Formula 5

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cycloalkyl groups. Lower alkenyl is defined similarly having 2 to 6 carbons for normal alkenyl, and 3 to 5 carbons for branch chained and cycloalkenyl groups.

The term "ester" as used here refers to and covers any compound falling within the definition of that term as classically used in organic chemistry. It includes organic and inorganic esters. Where B (of Formula 1) is —COOH, this term covers the products derived from treatment of this function with alcohols or thioalcohols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

The term "amides" has the meaning classically accorded that term in organic chemistry. In this instance it includes the unsubstituted amides and all aliphatic and aromatic mono- and di- substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula—CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compound in this invention having a functionality capable of forming such salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

Some of the compounds utilized in accordance with the present invention may have trans and cis (E and Z) isomers. In addition, the compounds of the present invention may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

With reference to the symbol Y in Formula 1, the preferred compounds of the invention are those where Y is phenyl, pyridyl, thienyl or furyl. Even more preferred are compounds where Y is phenyl or pyridyl. As far as substitutions on the Y (phenyl) and Y (pyridyl) groups are concerned, compounds are preferred where the phenyl group is 1,4 (para) substituted, and where the pyridine ring is 2,5 substituted. (Substitution in the 2,5 positions in the "pyridine" nomenclature corresponds to substitution in the 6-position in the "nicotinic acid" nomenclature.) The R$_3$ group of the aromatic or heteroaromatic ring Y is preferably hydrogen.

With reference to the symbol X in Formula 1, compounds are preferred in accordance with the invention where X is O, N-isopropyl, or $C(R_1)_2$, particularly where $C(R_1)_2$ is $C(CH_3)_2$. Generally speaking compounds are preferred where $R_1$ is hydrogen or methyl. The substituent $R_2$ in accordance with the present invention is preferably H or methyl. In the event X is $C(R_1)_2$ (tetrahydronaphthalene compounds) then the $R_2$ substituent preferably occupies the 3-position of the 5,6,7,8-tetrahydronaphthalene nucleus. When X is O, S or $NR_1$ (chroman, thiochroman or tetrahydroquinoline derivatives) then the R2 substituent preferably occupies the 7-position of the chroman, thiochroman or tetrahydroquinoline nucleus.

The $R_4$ group of the imine function (represented by M in Formula 1) of the compounds of the invention is preferably hydrogen or methyl. When X is $C(R_1)_2$ (tetrahydronaphthalene compounds) then the M substituent preferably occupies the 2-position of the 5,6,7,8-tetrahydronaphthalene nucleus. When X is O, S or $NR_1$ (chroman, thiochroman or tetrahydroquinoline derivatives) then the M substituent preferably occupies the 6-position of the chroman, thiochroman or tetrahydroquinoline nucleus.

Referring now to the A–B group of Formula 1, compounds are preferred in accordance with the invention where A is $(CH_2)_n$ where n is 0 to 3, and even more preferred where n is 0. B is preferably COOH (carboxylic acid or salt thereof), $COOR_8$ (ester), or $CONR_9R_{10}$ (amide).

The most preferred compounds of the invention are listed in Table I with reference to Formulas 6 and 7.

TABLE 1

Compounds of Formula 6

| Compound # | $R_1,R_1$ | X | $R_2$ | $R_4$ | Z | $R_8$ |
|---|---|---|---|---|---|---|
| 1 | H,H | $C(CH_3)_2$ | H | H | CH | $CH_3$ |
| 2 | H,H | $C(CH_3)_2$ | H | H | CH | H |
| 3 | H,H | $C(CH_3)_2$ | $CH_3$ | H | CH | H |
| 4 | H,H | $C(CH_3)_2$ | H | H | CH | $C_2H_5$ |
| 5 | H,H | $C(CH_3)_2$ | H | $CH_3$ | CH | $C_2H_5$ |
| 6 | H,H | $C(CH_3)_2$ | $CH_3$ | H | CH | $C_2H_5$ |
| 7 | H,H | $C(CH_3)_2$ | H | H | N | $C_2H_5$ |
| 8 | O | N-i-propyl | H | H | CH | $C_2H_5$ |

Compounds of Formula 7

| Compound # | $R_1,R_1$ | X | $R_2$ |
|---|---|---|---|
| 9 | H,H | $C(CH_3)_2$ | H |
| 10 | $CH_3,CH_3$ | O | H |
| 11 | H,H | $C(CH_3)_2$ | $CH_3$ |

Formula 6

Formula 7

The compounds of this invention may be administered systemically or topically, depending on such considerations as the condition to be treated, need for site-specific treatment, quantity of drug to be administered, and numerous other considerations. In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many disease for which these compounds are useful.

The retinoic acid-like activity of these compounds is confirmed through the classic measure of retinoic acid activity involving the effects of retinoic acid on ornithine decarboxylase. The original work on the correlation between retinoic acid and decrease in cell proliferation was done by Verma & Boutwell, Cancer Research, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-O-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. Activity of exemplary compounds of the present invention in the above-described ODC assay is disclosed in Table 2 which provides the $IC_{80}$ concentration for the respective exemplary compound. ("$IC_{80}$" is that concentration of the test compound which causes 80% inhibition in the ODC assay)

TABLE 2

| Compound # | $IC_{80}$ conc (nmols) |
|---|---|
| 1 | 14.5 |
| 4 | 2.5 |
| 5 | 5.5 |
| 6 | 293 |
| 7 | >30 |
| 9 | 9.6 |
| 10 | 44.0 |
| 11 | 3.5 |

Specific Embodiments

The compounds of this invention can be made by the synthetic chemical pathways illustrated here. The synthetic chemist will readily appreciate that the conditions set out here are specific embodiments which can be generalized to any and all of the compounds represented by Formula 1. Generally speaking, the compounds of the present invention are imines of unique chemical structure, which are synthesized by the reaction of an aldehyde or ketone with a primary amine. Reaction Scheme I illustrates in general terms synthesis of those compounds of the present invention which are derived from a primary amine of Formula 2, and Reaction Scheme 2 illustrates synthesis of those compounds of the invention which are derived from a ketone or aldehyde of Formula 4. In other words, Reaction Scheme I illustrates synthesis of those compounds of Formula I where the symbol M represents —N=CR$_4$—. These compounds are represented by Formula 8 in the reaction scheme. Reaction Scheme 2 illustrates synthesis of those compounds of Formula 1 where the symbol M represents —R$_4$C=N—. The latter compounds are represented by Formula 9 in the reaction scheme. The reactions illustrated in these schemes are usually conducted in an anhydrous inert solvent, such as dichloromethane, benzene, or tetrahydrofuran, at room temperature or under reflux conditions, in the presence of a drying agent, such as molecular sieves or anhydrous magnesium sulfate. The imine product of the reaction can typically be obtained by evaporation of the solvent, followed by crystallization or chromatography.

Reaction Scheme 1

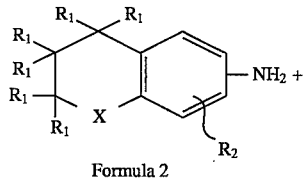

Formula 2

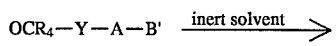

Formula 3

-continued
Reaction Scheme 1

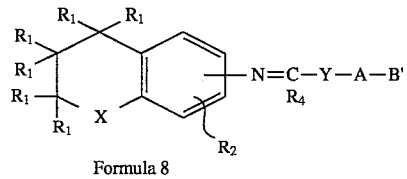

Formula 8

Reaction Scheme 2

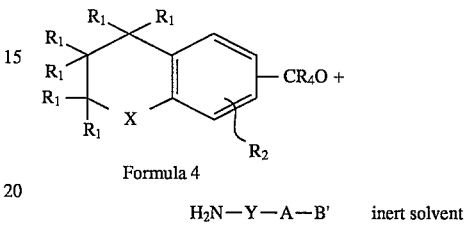

Formula 9

Generally speaking the starting material primary amines and aldehydes or ketones, that is the respective compounds of Formula 2, 5, 3 and 4 are available commercially or can be obtained in accordance with procedures described in the chemical literature. For example, 2-amino-5,6,7,8-tetrahydro-5,5,8,8-tetramethylnaphthalene (2-aminotetramethyltetralin, Compound 20) can be obtained in accordance with the procedure described in the article Journal of Medicinal Chemistry, 1988, 31, 2182–2193 (Kagechika et al.) which is incorporated herein by reference. This reagent (Compound 20) is used for the synthesis of exemplary Compounds 1, 2, 4, 5 and 7. The corresponding 3-methyl compound (2-amino-5,6,7,8-tetrahydro-3,5,5,8,8-pentamethylnaphthalene Compound 21) can also be obtained in accordance with the Kagechika et al. reference. This compound is utilized in the synthesis of exemplary compounds 3 and 6 of the present invention.

5,6,7,8-Tetrahydro-5,5,8,8-tetramethylnaphthalene-2-carboxyaldehyde (Compound 22) is used as starting material for the synthesis of exemplary Compound 9 of the present invention. Compound 22 can be obtained in accordance with the procedure of Journal of Medicinal Chemistry, 1989, 32, p1098 (Kagechika et al. II), incorporated herein by reference. 5,6,7,8-Tetrahydro-3,5,5,8,8-pentamethylnaphthalene-2-carboxyaldehyde (Compound 23) is used for the synthesis of exemplary Compound 11 of the present invention. Compound 23 can be obtained in accordance with U.S. Pat. No. 4,950,369, the specification of which is incorporated herein by reference.

2,2,4,4-tetramethyl-6-chromanaldehyde (Compound 24) is used in the condensation reaction which produces exemplary Compound 10 of the present invention. Compound 24 is obtained by reduction of 2,2,4,4-tetramethyl-chroman-6-carboxylic acid and subsequent oxidation of the resulting primary alcohol. 2,2,4,4-tetramethyl-6-chromanaldehyde (Compound 24) is described in U.S. Pat. No. 5,006,550, the specification of which is incorporated here by reference.

Methyl 4-formylbenzoate (Compound 25), 4-carboxybenzaldehyde (Compound 26) 4-carboxyacetophenone (Compound 27) and ethyl 4-formylbenzoate (Compound 28) are reagents corresponding to Formula 3 in accordance with Reaction Scheme 1, and are used for the synthesis of exemplary Compounds 1–6 and 8 of the present invention. Compounds 25, 26 and 27 are available from Aldrich Chemical Co., and Compound 28 can be obtained in accordance with Journal of Medicinal Chemistry 1981, 24, p583 (Dawson et al.) incorporated herein by reference.

Ethyl 4-aminobenzoate (Compound 29) is a commercially available reagent (Aldrich) which is represented by Formula 5 in Reaction Scheme 2 and is used for preparing exemplary Compounds 9–11 of the present invention.

Further examples of compounds represented by Formula 2 which can be used in the condensation reactions with compounds of Formula 3 to provide additional compounds of the invention are as follows:

2-amino-5,6,7,8-tetrahydro-5,5,8,8-tetramethyl-3-ethylnaphthalene;

2-amino-5,6,7,8-tetrahydro-5,5,8,8-tetramethyl-3-propylnaphthalene;

2-amino-5,6,7,8-tetrahydro-5,5,8,8-tetramethyl-3-chloronaphthalene;

2-amino-5,6,7,8-tetrahydro-5,5,8,8-tetramethyl-3-bromonaphthalene;

3-amino-5,6,7,8-tetrahydro-5,5,8,8-tetramethylnaphthalene;

3-amino-5,6,7,8-tetrahydro-2,5,5,8,8-pentamethylnaphthalene;

3-amino-5,6,7,8-tetrahydro-5,5,8,8-tetramethyl-2-ethylnaphthalene;

3-amino-5,6,7,8-tetrahydro-5,5,8,8-tetramethyl-2-propylnaphthalene;

3-amino-5,6,7,8-tetrahydro-5,5,8,8-tetramethyl-2-chloronaphthalene;

3-amino-5,6,7,8-tetrahydro-5,5,8,8-tetramethyl-2-bromonaphthalene;

6-amino-4,4-dimethylchroman;
6-amino-4,4,7-trimethylchroman;
6-amino-2,2,4,4-tetramethylchroman;
6-amino-2,2,4,4,7-pentamethylchroman;
7-amino-4,4-dimethylchroman;
7-amino-4,4,6-trimethylchroman;
7-amino-2,2,4,4-tetramethylchroman;
7-amino-2,2,4,4,6-pentamethylchroman;
6-amino-4,4-dimethylthiochroman;
6-amino-4,4,7-trimethylthiochroman;
6-amino-2,2,4,4-tetramethylthiochroman;
6-amino-2,2,4,4,7-pentamethylthiochroman;
7-amino-4,4-dimethylthiochroman;
7-amino-4,4,6-trimethylthiochroman;
7-amino-2,2,4,4-tetramethylthiochroman;
7-amino-2,2,4,4,6-pentamethylthiochroman;
6-amino-4,4-dimethyl-1,2,3,4-tetrahydroquinoline;
6-amino-4,4,7-trimethyl-1,2,3,4tetrahydroquinoline;
6-amino-2,2,4,4-tetramethyl-1,2,3,4tetrahydroquinoline;
6-amino-2,2,4,4,7-pentamethyl-1,2,3,4tetrahydroquinoline;
7-amino-4,4-dimethyl-1,2,3,4-tetrahydroquinoline;
7-amino-4,4,6-trimethyl-1,2,3,4tetrahydroquinoline;
7-amino-2,2,4,4-tetramethyl-1,2,3,4tetrahydroquinoline;
7-amino-2,2,4,4,6-pentamethyl-1,2,3,4-trahydroquinoline;

Further examples of compounds of Formula 3 are:
methyl 6-carboxynicotinate;
nicotinic acid 6-carboxaldehyde;
3-carboxy-thiophene-5-carboxaldehyde;
3-methoxycarbonyl-thiophene-5-carboxaldehyde;
3-ethoxycarbonyl-thiophene-5-carboxaldehyde;
2-carboxy-thiophene-5-carboxaldehyde;
2-methoxycarbonyl-thiophene-5-carboxaldehyde;
2-ethoxycarbonyl-thiophene-5-carboxaldehyde;
3-carboxy-furan-5-carboxaldehyde;
3-methoxycarbonyl-furan-5-carboxaldehyde;
3-ethoxycarbonyl-furan-5-carboxaldehyde;
2-carboxy-furan-5-carboxaldehyde;
2-methoxycarbonyl-furan-5-carboxaldehyde;
2-ethoxycarbonyl-furan-5-carboxaldehyde;

Still further, additional examples of compounds represented by Formula 4 which can be used in the condensation reactions with compounds of Formula 5 to provide additional compounds of the invention are as follows:

5,6,7,8-tetrahydro-5,5,8,8-tetramethyl-3-ethylnaphthalene-2-carboxaldehyde;

5,6,7,8-tetrahydro-5,5,8,8-tetramethyl-3-propylnaphthalene-2-carboxaldehyde;

5,6,7,8-tetrahydro-5,5,8,8-tetramethyl-3-chloronaphthalene-2-carboxaldehyde;

5,6,7,8-tetrahydro-5,5,8,8-tetramethyl-3-bromonaphthalene-2-carboxaldehyde;

5,6,7,8-tetrahydro-5,5,8,8-tetramethylnaphthalenecarboxaldehyde;

5,6,7,8-tetrahydro-2,5,5,8,8-pentamethylnaphthalene-3-carboxaldehyde;

5,6,7,8-tetrahydro-5,5,8,8-tetramethyl-2-ethylnaphthalene-3-carboxaldehyde;

5,6,7,8-tetrahydro-5,5,8,8-tetramethyl-2-propylnaphthalene-3-carboxaldehyde;

5,6,7,8-tetrahydro-5,5,8,8-tetramethyl-2-chloronaphthalene-3-carboxaldehyde;

5,6,7,8-tetrahydro-5,5,8,8-tetramethyl-2-bromonaphthalene-3-carboxaldehyde;

4,4-dimethylchroman-6-carboxaldehyde;
4,4,7-trimethylchroman-6-carboxaldehyde;
2,2,4,4,7-pentamethylchroman-6-carboxaldehyde;
4,4-dimethylchroman-7-carboxaldehyde;
4,4,6-trimethylchroman-7-carboxaldehyde;
2,2,4,4-tetramethylchroman-7-carboxaldehyde;
2,2,4,4,6-pentamethylchroman-7-carboxaldehyde;
4,4-dimethylthiochroman-6-carboxaldehyde;
4,4,7-trimethylthiochroman-6-carboxaldehyde;
2,2,4,4-tetramethylthiochroman-6-carboxaldehyde;
2,2,4,4,7-pentamethylthiochroman-6-carboxaldehyde;
4,4-dimethylthiochroman-7-carboxaldehyde;
4,4,6-trimethylthiochroman-7-carboxaldehyde;
2,2,4,4-tetramethylthiochroman-7-carboxaldehyde;
2,2,4,4,6-pentamethylthiochroman-7-carboxaldehyde;
4,4-dimethyl-1,2,3,4-tetrahydroquinoline-6-carboxaldehyde;

4,4,7-trimethyl-1,2,3,4-tetrahydroquinoline-6-carboxaldehyde;

2,2,4,4-tetramethyl-1,2,3,4-tetrahydroquinoline-6-carboxaldehyde;

2,2,4,4,7-pentamethylmethyl-1,2,3,4-tetrahydroquinoline-6-carboxaldehyde;

4,4-dimethyl-1,2,3,4-tetrahydroquinoline-7-carboxaldehyde;

4,4,6-trimethyl-1,2,3,4-tetrahydroquinoline-7-carboxaldehyde;

2,2,4,4-tetramethyl-1,2,3,4-tetrahydroquinoline-7-carboxaldehyde;

2,2,4,4,6-pentamethyl-1,2,3,4-tetrahydroquinoline-7-carboxaldehyde;

Compounds of Formula 5:

methyl 6-aminonicotinate;

6-amino-nicotinic acid;

2-amino-thiophene-4-carboxylic acid;

methyl 2-amino-thiophene-4-carboxylate;

ethyl 2-amino-thiophene-4-carboxylate;

2-amino-thiophene-5-carboxylic acid;

methyl 2-amino-thiophene-5-carboxylate;

ethyl 2-amino-thiophene-5-carboxylate;

2-amino-furan-4-carboxylic acid;

methyl 2-amino-furan-4-carboxylate;

ethyl 2-amino-furan-4-carboxylate;

2-amino-furan-5-carboxylic acid;

methyl 2-amino-furan-5-carboxylate;

ethyl 2-amino-furan-5-carboxylate.

Reaction Scheme 3

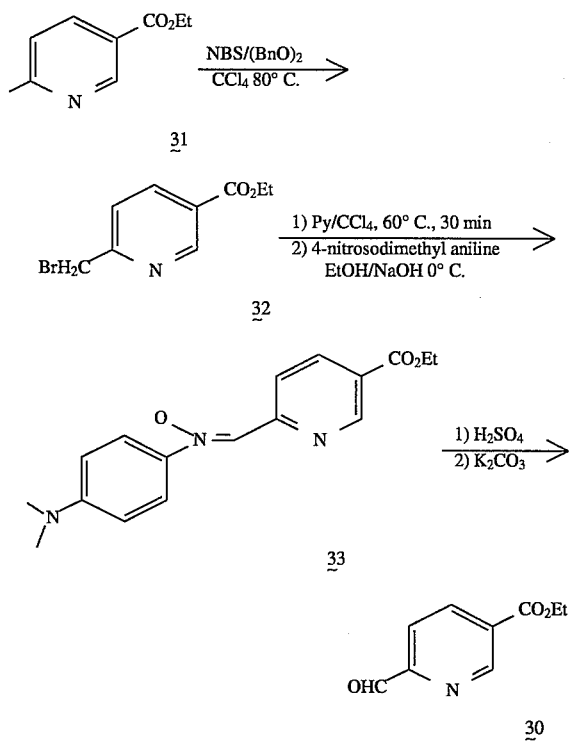

The reagent ethyl 6-carboxynicotinate (Compound 30) is used for the synthesis of exemplary Compound 7 of the present invention. Compound 30 is obtained in accordance with Reaction Scheme 3, wherein ethyl 6-methylnicotinate (Compound 31, available from Aldrich) is reacted with N-bromosuccinimide and benzoylperoxide to yield ethyl 6-bromomethylnicotinate (Compound 32). The latter compound is reacted with pyridine and subsequently with N,N-dimethyl-4-nitrosoaniline and base to provide 4-ethoxycarbonyl-6-pyridylaldehyde N-(4-dimethylamino)phenyl oxime (Compound 33), which is subsequently hydrolyzed to yield ethyl 6-carboxynicotinate (Compound 30).

Reaction Scheme 4

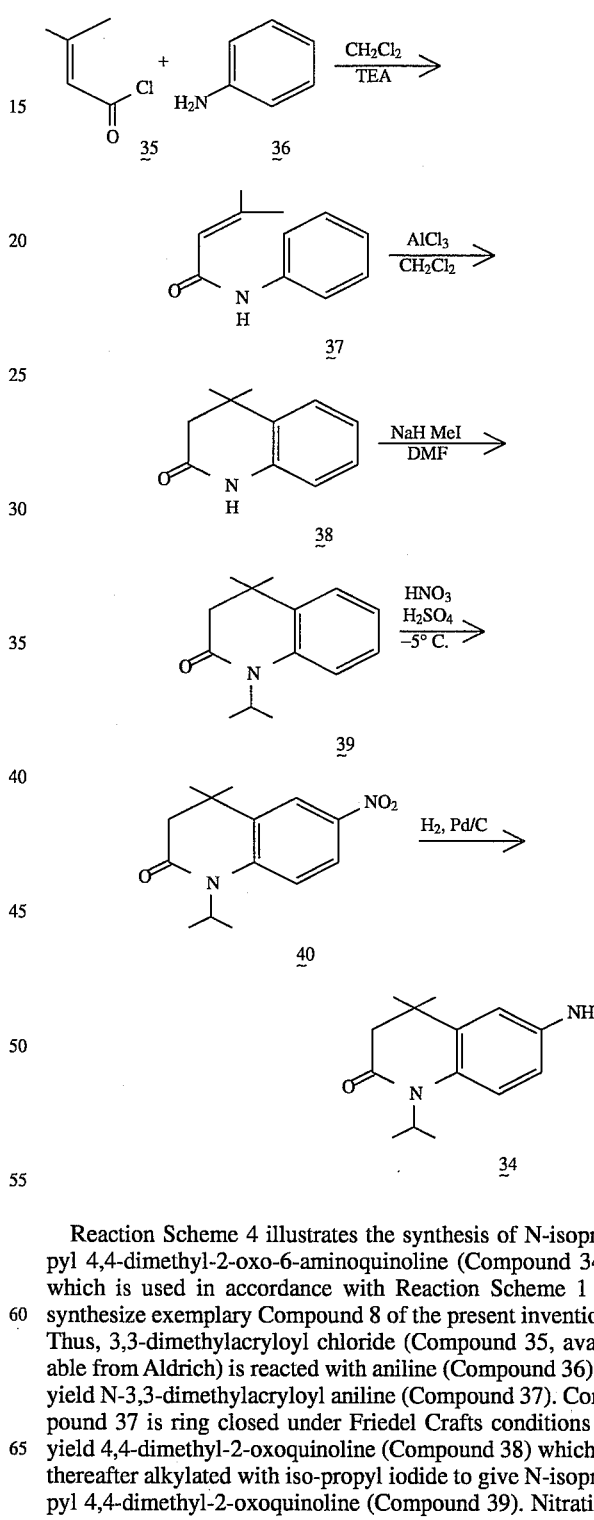

Reaction Scheme 4 illustrates the synthesis of N-isopropyl 4,4-dimethyl-2-oxo-6-aminoquinoline (Compound 34), which is used in accordance with Reaction Scheme 1 to synthesize exemplary Compound 8 of the present invention. Thus, 3,3-dimethylacryloyl chloride (Compound 35, available from Aldrich) is reacted with aniline (Compound 36) to yield N-3,3-dimethylacryloyl aniline (Compound 37). Compound 37 is ring closed under Friedel Crafts conditions to yield 4,4-dimethyl-2-oxoquinoline (Compound 38) which is thereafter alkylated with iso-propyl iodide to give N-isopropyl 4,4-dimethyl-2-oxoquinoline (Compound 39). Nitration of Compound 39 yields N-isopropyl 4,4-dimethyl-2-oxo-6-nitroquinoline Compound 40, which is reduced with hydrogen on palladium to give Compound 34.

As it is apparent from the foregoing, the reagents of Formulas 2–5 which give rise to the compounds of the present invention are either known compounds, or can be synthesized in synthetic routes generally within the skill of the art. Compounds of the invention in accordance with Formula 1 can also be subjected to certain synthetic conversions or transformations, which produce still further compounds of the invention. Alternatively, blocked or protected derivatives of the compounds of the invention may be obtained in accordance with Reaction Schemes 1 and 2, and such blocked or protected derivatives can be converted into compounds of the invention in chemical reactions well known in the art. Such known chemical reactions can also be routinely utilized for the synthesis of the reagents of Formulas 2–5. In connection with the foregoing the following well known and published synthetic methodology is noted.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and Protecting Groups, Ed. Greene, John Wiley & Sons, 1981.

To increase the value of n in the compounds of Formula 3 and 5 before affecting the condensation reaction of Reaction Schemes 1 and 2 (where such compounds corresponding to Formula 3 and 5 are not available from a commercial source) aromatic or heteroaromatic carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph.

Compounds of Formula 3, or of Formula 5 where A is an alkenyl group having one or more double bonds can be made for example, by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of Formula 3 or of Formula 5 where the A group has a triple (acetylenic) bond can be made by reaction of a corresponding aromatic-methyl ketone with strong base, such as lithium diisopropyl amide.

The acids and salts derived from compounds of Formula 3 or of Formula 5 or in appropriate cases of Formula 1, are readily obtainable from the corresponding esters. Basic saponification with an alkali metal base will provide the acid. For example, an ester may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 50 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of Formula 3 or of Formula 5 where B is H can be prepared from the corresponding halogenated aromatic or hetero aromatic compounds, preferably where the halogen is I.

The following specific examples further illustrate the invention and describe the best mode thereof.

Specific Examples

N-3,3-Dimethylacryloyl Aniline (Compound 37)

In a 100 mL round bottom flask was placed NaH (1.93 g, 0.05 mol). After washing with dry hexane (2×10 mL dry THF (15 mL) was added), to this tan solid. Then, the resulting suspension was added to a solution of aniline (Compound 36, 4.89 mL, 0.054 mol) in dry THF (7 mL) at 0° C. After stirring for 30 min, 3,3-dimethylacryloyl chloride (Compound 35, 6.56 mL, 0.059 mol) was added dropwise to the above solution. The reaction mixture was stirred under $N_2$ for overnight followed by a slow addition of water. The mixture was extracted with ethyl acetate (2×20 mL). The combined organic layers were washed with $NH_4Cl$ (sat.) and NaCl (sat.), dried over $MgSO_4$ and concentrated to give the title compound as a tan solid (4.45 g, 51%). $^1H$ NMR d 1.87 (s, 3H), 2.21 (s, 3H), 5.72 (s, 1H), 7.29–7.56 (m, 5H).

4,4-Dimethyl-2-oxoquinoline (Compound 38)

To a 500 mL round bottom flask containing $AlCl_3$ (5.22 g, 0.039 mol) was added dry $CH_2Cl_2$ (40 mL). Then a solution of N-(3,3-dimethylacryloyl) aniline (Compound 37, 4.45 g, 0.025 mol) in $CH_2Cl_2$ (50 mL) was added slowly. The reaction mixture was stirred at room temperature for overnight followed by the addition of ice-cubes. This mixture was extracted with ethyl acetate (2×20 mL). The combined organic layers were washed with NaCl (sat.), dried over $MgSO_4$ and concentrated to give a brownish oil. Purification of this oil by column chromatography (10% ethyl acetate in hexane) gave the title compound as a light yellow solid (2.31 g, 52%). $^1H$ NMR d 1.34 (s, 6H), 2.51 (s, 2H), 6.85 (d, J=7.8 Hz, 1H), 7.29 (d, J=7.6 Hz, 1H), 7.03–7.08 (m, 1H), 7.16–7.23 (m, 1H), 9.01 (b, 1H).

N-Isopropyl 4,4-dimethyl-2-oxoquinoline (Compound 39)

To a suspension of NaH (0.121 g, 3.0 mmol) in dry DMF (2 mL) was added a solution of 4,4,-dimethyl-2-oxoquinoline (Compound 38, 0.529 g, 3.0 mmol) in dry DMF (10 mL). The mixture was stirred at room temperature for 30 min followed by addition of isopropyl iodide. The reaction mixture was left at room temperature for 72 h. Then ice-cubes were added to the reaction and the mixture was extracted with ethyl acetate (2×5 mL). The combined organic layers were washed with saturated solution of NaCl, dried over $MgSO_4$ and concentrated to give a pale yellow oil. Purification by column chromatography (silica gel, 30% ethyl acetate in hexane) yielded the title compound as a colorless oil (472 mg, 72%). $^1H$ NMR d 1.32 (s, 6H), 1.57 (d, J=7.1 Hz, 6H), 2.45 (s, 2H), 4.74 (q, J=7.0 Hz, 1H), 7.06–7.32 (m, 4H).

N-Isopropyl 4,4-dimethyl-2-oxo-6-nitroquinoline (Compound 40)

N-Isopropyl 4,4,-dimethyl-2-oxo-quinoline (Compound 39, 472 mg, 2.18 mmol) was added dropwise to $H_2SO_4$ (con. 0.3 mL) cooled to −5° C. with a salt-ice bath. To this brown oil was added a mixture of $HNO_3$ (0.16 mL) and $H_2SO_4$ (0.65 mL) at a rate so slow that the internal temperature did not exceed 0° C. The resulting dark oil was stirred vigorously for 10 minutes, followed by addition of ice-water. The yellow reaction mixture was extracted with ethyl acetate (2×5 mL). The combined organic layers were washed with $NaHCO_3$ (10%), dried over $MgSO_4$ and concentrated to give yellow solids. $^1H$ NMR d 1.34 (s, 6H), 1.53(d, J=6.8 Hz, 6H), 2.48 (s, 2H), 4.70–4.79 (m, 1H), 7.25 (d, J= 6.3 Hz, 1H), 8.10–8.15 (m, 2H).

N-Isopropyl 4,4-dimethyl-2-oxo-6-aminoquinoline (Compound 34)

N-Isopropyl 4,4,-dimethyl-2-oxo-6-nitroquinoline (Compound 40, 220 mg, 0.84 mmol) was dissolved in $CH_3OH$ (3 ml). The solution was cleansed by flushing with $N_2$ gas, and thereafter a catalytic amount of 10% Pd/C was added. The resulting mixture was hydrogenated at room temperature for 5 hours. After evaporation of the solvent the title compound was obtained in quantitative yield as a light purple oil. (184.2 mg 94%) $^1H$ NMR d 1.23 (s, 6H), 1.49 (d, J=7.0 Hz, 6H), 2.36 (s, 2H), 4.68 (q, J=7.0 Hz, 1H), 6.55 (dd, J1=2.8 Hz, $J_2$= 8.6 Hz, 1H), 6.64 (d, J=2.6 Hz, 1H), 6.94 (d, J=8.6 Hz, 1H).

Ethyl 6-bromomethyl nicotinate (Compound 32)

A mixture of ethyl 6-methylnicotinate (Compound 31, 0.473 g, 2.87 mmol), N-bromosuccinimide (561 mg, 3.15 mmol) and benzoyl peroxide (0.007 g, 0.03 mmol) in $CCl_4$ (20 mL) was refluxed for overnight. The reaction mixture was concentrated and the residue was purified by column chromatography with 20% ethyl acetate in hexane to yield the title compound as a colorless oil (0.65 g, 93%). $^1H$ NMR d 1.42 (t, J=7.1 Hz, 3H), 4.43 (q, J=7.1 Hz, 2H), 4.59 (s, 2H), 7.52 (d, J=8.3 Hz, 1H), 8.29 (dd, $J_1$=2.1 Hz, $J_2$=8.7 Hz, 1H), 9.18 (d, J=2.1 Hz, 1H).

4-Ethoxycarbonyl-6-pyridylaldehyde N-(4-dimethylamino)phenyl oxime (Compound 33)

A mixture of ethyl 6-bromomethyl nicotinate (Compound 32, 0.65 g, 2.65 mmol) and pyridine (0.23 g, 2.91 mmol) in $CCl_4$ (5 mL) was heated at 70° C. for 30 min. The solvent was evaporated and the residual dark-red oil was dissolved in EtCH (20 mL). To this dark colored solution was added a solution of N,N-dimethyl-4-nitroso aniline (0.438 g, 2.91 mmol) in EtCH (5 mL). This solution was chilled to 0° C. and an aqueous solution of NaOH (1N, 2.7 mL) was added dropwise. After stirring at 0° C. for 1 hour, the reaction mixture was concentrated. The residue was dissolved in water and extracted with ethyl acetate. The organic layer was dried, concentrated and the resulting red oil was purified by column chromatography (silica gel, 30% ethyl acetate in hexane) to give the title compound as a red solid. $^1H$ NMR d 1.45 (t, J= 7.1 Hz, 3H), 4.46 (q, J=7.1 Hz, 2H), 3.06 (s, 6H), 6.71 (d, J=9.3 Hz, 2H), 7.75 (d, J=9.3 Hz, 2H), 8.32 (s, 1H), 8.41 (dd, $J_1$=2.1 Hz, $J_2$=8.6 Hz, 1H), 9.24 (d, J=2.1 Hz, 1H), 9.38 (d, J=8.7 Hz, 1H).

Ethyl 6-Carboxynicotinate (Compound 30)

4-Ethoxycarbonyl-6-pyridylaldehyde N-(4-dimethylamino)phenyl oxime (Compound 33, 110 mg, 0.35 mmol) was added slowly to a chilled mixture of $H_2SO_4$ (1N, 10 mL) and ethyl ether (10 mL). The mixture was stirred at 0° C. for 1 hour followed by addition of an aqueous solution of NaOH until the pH of the aqueous phase reached 8. The mixture was extracted with ethyl acetate (3×10 mL), and the combined organic extracts were dried and concentrated to give the title compound as a yellow solid. (51 mg, 81%) $^1H$ NMR d 1.44 (t, J= 7.1 Hz, 3H), 4.44 (q, J=7.1 Hz, 2H), 8.27 (d, J=8.2 Hz, 1H), 8.36 (d, J=8.3 Hz, 1H), 8.72 (s, 1H), 9.25 (s, 1H).

2,2,4,4-Tetramethyl-6-chroman aldehyde (Compound 24)

To a solution of 2,2,4,4-tetramethylchroman 6-carboxylic acid (0.28 g, 1.2 mmol) in THF (5 ml) under $N_2$ was added 1M of $LiALH_4$/THF (1.15 ml, 1.15 mmol). The reaction mixture was left at room temperature for overnight, followed by addition of ice-water to the reaction. The reaction mixture was extracted with ethyl acetate, the organic extracts were dried and concentrated to give 2,2,4,4-tetramethyl-chroman-6-yl methanol as a white solid. Without further purification, the alcohol was dissolved in $CH_2Cl_2$ (5 ml) and $MnO_2$ (1.04 g, 12 mmol) was added. The resulting mixture was stirred at room temperature for 5 hours. After filtration, the resulting colorless clear solution was concentrated and purified by column chromatography (silica gel, 10% ethyl acetate in hexane) to give the title compound as a colorless oil (0.147 g, 57%). $^1H$ NMR d 1.39 (d, 12H), 1.88 (s, 2H), 6.89 (d, J=8.4 Hz, 1H), 7.62 (dd, J₁=2.0 Hz, J₂= 8.4 Hz, 1H), 7.85 (d, J=2.0 Hz, 1H), 9.86 (s, 1H).

N-(5,6,7,8-Tetrahydro-5,5,8,8-tetramethyl-2-naphthalenyl 4-methoxycarbonyl benzaldimine (Compound 1)

To a solution of 2-amino-5,6,7,8-tetrahydro-5,5,8,8-tetramethylnaphthalene (Compound 20, 0.086 g, 0.42 mmol) in dry dichloromethane (5 mL) was added 4-methoxycarbonyl benzaldehyde (Compound 25, 0.075 g, 0.42 mmol). The reaction mixture was stirred at room temperature for 30 min and then concentrated under vacuum to yield a yellow oil. Purification of the desired imine by flash column chromatography (silica gel, 20% ethyl acetate in hexane) yielded yellow solids (0.143 g, 97%) which were recrystallized from $CH_2Cl_2$/hexane to give the title compound as yellow crystals (107 mg, 69%). $^1$H NMR d 1.32 (d, J=8.0 Hz, 12H), 1.71 (s, 4H), 3.95 (s, 3H), 7.03 (dd, J₁=2.1 Hz, J₂=8.3 Hz, 1H), 7.22 (d, J=2.3 Hz, 1H), 7.35 (d, J=8.3 Hz, 1H), 7.97 (d, J=8.4 Hz, 2H), 8.14 (d, J=8.3 Hz, 2H), 8.54 (s, 1H).

N-(5,6,7,8-Tetrahydro-5,5,8,8-tetramethyl)-2-naphthalenyl 4-carboxy benzaldimine (Compound 2)

A solution of 2-amino-5,6,7,8-tetrahydro-5,5,8,8-tetramethylnaphthalene (Compound 20, 0.106 g, 0.52 mmol) together with 4-carboxybenzaldehyde (Compound 26, 0.071 g, 0.47 mmol) in THF (5.0 ml) was stirred at room temperature in the presence of $MgSO_4$ for 2 days. The reaction mixture was filtered through celite and the clear yellow solution was concentrated under reduced pressure to give yellow solids. The solids were successively washed with hexane until no tetramethyltetralin amine presented in the hexane layer (checked by TLC). The title compound was obtained as a light yellow solid (0.093 g, 60%). $^1$H NMR d 1.32 (d, 12H), 1.72 (s, 4H), 7.06 (dd, J₁=2.2 Hz, J₂=8.4 Hz, 1H), 7.24 (d, J=2.2 Hz, 1H), 7.36 (d, J=8.3 Hz, 1H), 8.01 (d, J=8.4 Hz, 2H), 8.21 (d, J=8.4 Hz, 2H), 8.56 (s, 1H).

N-(5,6,7,8-Tetrahydro-3,5,5,8,8-pentamethyl)-2-naphthalenyl 4-carboxy benzaldimine (Compound 3)

A solution of 2-amino-5,6,7,8-tetrahydro-3,5,5,8,8-pentamethylnaphthalene 2-aminopentamethyltetralin, (Compound 21, 0.088 g, 0.41 mmol) together with 4-carboxybenzaldehyde (Compound 0.052 g, 0.34 mmol) in THF (5.0 ml) was stirred at room temperature in the presence of $MgSO_4$ for 2 days. The reaction mixture was filtered through celite and the clear yellow solution was concentrated under reduced pressure to give yellow solids. The yellow solids were washed with hexane until no 2-aminopentamethyltetralin appeared in the hexane layer (checked by TLC). The title compound was obtained as light yellow crystals (70 mg, 59%). $^1$H NMR d 1.31 (d, 12H), 1.70 (s, 4H), 2.34 (S, 3H), 6.88 (s, 1H), 7.17 (s, 1H), 8.03 (d, J= 8.4 Hz, 2H), 8.23 (d, J=8.4 Hz, 2H), 8.45 (s, 1H)

N-(5,6,7,8-Tetrahydro-5,5,8,8-tetramethyl)-2-naphthalenyl 4-ethoxycarbonyl benzaldimine (Compound 4)

A solution of 2-amino-5,6,7,8-tetrahydro-5,5,8,8-tetramethylnaphthalene (Compound 20, 0.088 g, 0.43 mmol) and ethyl 4-carboxybenzoate (Compound 28 0.077 g, 0.43 mmol) in $CH_2Cl_2$ (3.0 ml) was stirred at room temperature in the presence of $MgSO_4$ for 12 h. After concentration, the reaction mixture was purified by flash column chromatography (silica gel, 10% ethyl acetate in hexane) to yield yellow solids. These were recrystallized from 10% ethyl acetate in hexane to give the title compound as pale yellow crystals (0.081 g, 52%). $^1$H NMR d 1.32 (d, 12H), 1.43 (t, J=7.2 Hz, 3H), 4.42 (q, J=7.1 Hz, 2H), 7.04 (dd, J₁=2.3 Hz, J₂=8.4 Hz, 1H), 7.23 (d, J=2.0 Hz, 1H), 7.35 (d, J =8.4 Hz, 1H), 7.97 (d, J=8.4 Hz, 2H), 8.14 (d, J= 8.2 Hz, 2H), 8.54 (s, 1H).

N-(5,6,7,8-Tetrahydro-5,5,8,8-tetramethyl)-2-naphthalenyl 4-ethoxycarbonyl acetophenone imine (Compound 5)

A solution of 2-amino-5,6,7,8-tetrahydro-5,5,8,8-tetramethylnaphthalene (Compound 20, 0,137 g, 0.67 mmol) together with ethyl 4-carboxyacetophenone (Compound 27, 0.12 g, 0.67 mmol) in benzene (anh. 10.0 ml) was stirred under reflux for 12 h in the presence of molecular sieves. The solvent was evaporated under reduced pressure. Purification of the resulting yellow gummy mixture by flash column chromatography (silica gel, 20% ethyl acetate in hexane) yielded yellow solids. These were recrystallized from 10% ethyl acetate in hexane to give the title compound as pale yellow crystals (100 mg, 41%). $^1$H NMR d 1.29 (d, J= 5.0 Hz, 12H), 1.43 (t, J=7.1 Hz, 3H), 1.70 (s, 4H), 2.29 (s, 3H), 4.41 (q, J=7.1 Hz, 2H), 6.59 (dd, J₁= 2.2 Hz, J₂=8.2 Hz, 1H), 6.73 (d, J=2.1 Hz, 1H), 7.28 (d, J=8.7 Hz, 1H), 8.03 (d, J=8.1 Hz, 2H), 8.11 (d, J=8.5 Hz, 2H).

N-(5,6,7,8-Tetrahydro-3,5,5,8,8-pentamethyl)-2-naphthalenyl 4-ethoxycarbonyl benzaldimine (Compound 6)

A solution of 2-amino-5,6,7,8-tetrahydro-3,5,5,8,8-pentamethylnaphthalene (Compound 21, 0,040 g, 0.184 mmol) together with ethyl 4-carboxybenzoate (Compound 28, 0.033 g, 0,184 mmol) in $CH_2Cl_2$ (5.0 ml) was stirred at room temperature in the presence of $MgSO_4$ for 12 h. After concentration, the residue was purified by flash column chromatography (silica gel, 10% ethyl acetate in hexane) to yield the title compound as a yellow oil. (0.02 g, 30%). $^1$H NMR d 1.31 (d, 12H), 1.43 (t, J=7.2 Hz, 3H), 1.69 (s, 4H), 2.31 (s, 3H), 4.42 (q, J=7.1 Hz, 2H), 6.87 (s, 1H), 7.16 (s, 1H), 7.99 (d, J=8.4 Hz, 2H), 8.14 (d, J=8.3 Hz, 2H), 8.43 (s, 1H).

Ethyl 6-(N-5,6,7,8-tetrahydro-5,5,8,8-tetramethyl-2-naphthalenyl) 3-ethoxycarbonyl-pyridine-6-carboxaldehyde imine (Compound 7)

A solution of 2-amino-5,6,7,8-tetrahydro-5,5,8,8-tetramethylnaphthalene (Compound 20, 0.056g, 0.27 mmol) together with ethyl 6-carboxynicotinate (Compound 30, 0.048 g, 0.27 mmol) in $CH_2Cl_2$ (3.0 ml) was stirred at room temperature in the presence of $MgSO_4$ for 24 h. The reaction mixture was filtered through celite and the resulting clear yellow solution was concentrated under reduced pressure to give a yellow oil. Purification of this yellow oil by column chromatography (silica gel, 10% ethyl acetate in hexane) afforded the title compound as light yellow solids (0.070 g, 58%). $^1$H NMR d 1.32 (d, 12H), 1.45 (t, J=7.1 Hz, 3H), 1.71 (s, 4H), 4.46 (q, J=7.2 Hz, 2H), 7.14 (dd, J₁=2.2 Hz, J₂=8.4 Hz, 1H), 7.32 (d, J=2.2 Hz, 1H), 7.37 (d, J=8.4 HZ, 1H), 8.30 (d, J= 8.3 Hz, 1H), 8.40 (dd, J₁=2.2 Hz, J₂=8.2 Hz, 1H), 8.71 (s, 1H), 9.30 (d, J=2.2 Hz, 1H).

N-6-(N-Isopropyl-2-oxo-4,4-dimethyl) quinolinyl 4-ethoxycarbonyl benzaldimine (Compound 8)

A solution of N-isopropyl 4,4-dimethyl-2-oxo-6-amino-quinoline (Compound 34, 0.22 g, 0.95 mmol) together with 4-ethoxycarbonyl benzaldehyde (Compound 28, 0.169 g, 0.95 mmol) in $CH_2Cl_2$ (2.0 ml) was stirred at room temperature in the presence of $MgSO_4$ for 24 h. The reaction mixture was filtered through celite and the resulting clear yellow solution was concentrated under reduced pressure to give a yellow oil. Purification of this yellow oil by column chromatography (silica gel, 30% ethyl acetate in hexane) afforded the title compound as light yellow solids (0,255 g, 69%). $^1$H NMR d 1.32(s, 6H), 1.43 (t, J=7.1 Hz, 3H), 1.56 (d, J=7.0 Hz, 6H), 2.45 (s, 2H), 4.42 (q, J=7.2 Hz, 2H), 4.70–4.79 (m, 1H), 7.14 (dd, $J_1$=2.1 Hz, $J_2$=8.7 Hz, 1H), 7.18 (d, J=8.6 Hz, 1H), 7.25 (d, J=2.0 Hz, 1H), 7.98 (d, J=8.3 Hz, 2H), 8.15 (d, J=8.3 Hz, 2H), 8.55 (s, 1H).

N-(4'-Ethoxycarbonyl)phenyl 5,6,7,8-tetrahydro-5,5,8,8-tetramethyl,naphthalene-2-carboxaldehyde imine (Compound 9)

A solution of 5,6,7,8-tetrahydro-5,5,8,8-tetramethylnaphthalene-2-carboxaldehyde (Compound 22, 0.156 g, 0.72 mmol) together with ethyl 4-aminobenzoate (Compound 29, 0.238 g, 1.44 mmol) in dry benzene (2.0 ml) was refluxed in the presence of molecular sieves for a day and half. The solvent was evaporated under vacuum to give a yellow oil. Purification by flash column chromatography (silica gel, 10% ethyl acetate in hexane) yielded yellow solids which were further purified by recrystallization from $CH_2Cl_2$/hexane to yield the title compound as yellow needles. $^1$H NMR d 1.34 (d, J=8.6 Hz, 12H), 1.41 (t, J=7.1 Hz, 3H), 1.72 (s, 4H), 4.39 (q, J=7.0 Hz, 2H), 7.19 (d, J= 8.5 Hz, 2H), 7.43 (d, J=8.2 Hz, 1H), 7.68 (dd, $J_1$= 1.8 Hz, $J_2$=8.3 Hz, 1H), 7.83 (d, J=1.7 Hz, 1H), 8.07 (d, J=6.6 Hz, 2H), 8.38 (s, 1H).

N-(4'-Ethoxycarbonyl) phenyl 2,2,4,4-tetramethyl-chroman-6-carboxaldehyde imine (Compound 10)

A solution of ethyl 4-aminobenzoate (Compound 29, 0.057 g, 0.35 mmol) together with 2,2,4,4-tetramethyl 6-chroman aldehyde (Compound 24, 0.047 g, 0.216 mmol) in benzene (anh. 2.0 ml) was stirred under reflux for 12 h in the presence of molecular sieves. The solvent was evaporated under reduced pressure. Purification of the resulting yellow gummy mixture by flash column chromatography (silica gel, 20% ethyl acetate in hexane) yielded the title compound as yellow solids (0.066 g, 83%). $^1$H NMR d 1.41 (t, J=7.1 Hz, 3H), 1.41 (d, J=8.2 Hz, 12H), 1.89 (s, 2H), 4.39 (q, J= 7.1 Hz, 2H), 6.89 (d, J=8.4 Hz, 1H), 7.19 (d, J=8.5 Hz, 2H), 7.62 (dd, $J_1$=2.0 Hz, $J_2$=8.4 Hz, 1H), 7.88 (d, J=1.95 Hz, 1H), 8.07 (d, J=8.6 Hz, 2H), 8.34 (s, 1H).

N-(4'-Ethoxycarbonyl) phenyl-2-(5,6,7,8-tetrahydro-3,5,5,8,8-pentamethyl) naphthalene-2-carboxaldehyde imine (Compound 11)

A solution of 5,6,7,8-tetrahydro-3,5,5,8,8-pentamethyl-naphthalene-2-carboxaldehyde (Compound 23, 0.15 g, 0.65 mmol) together with ethyl 4-aminobenzoate (Compound 29, 0.118 g, 0.72 mmol) in benzene (2.0 ml) was stirred under reflux in the presence of molecular sieves for 24 h. The reaction mixture was filtered through celite and the clear yellow solution was concentrated under reduced pressure to give a yellow oil. Purification of this yellow oil by column chromatography (silica gel, 10% ethyl acetate in hexane) afforded the title compound as a light yellow oil (0.136 g, 55%). $^1$H NMR d 1.33 (d, 12H), 1.41 (t, J =7.1 Hz, 3H), 1.70 (s, 4H), 2.53 (s, 3H), 4.39 (q, J= 7.2 Hz, 2H), 7.17 (d, J=8.5 Hz, 2H), 7.17 (s, 1H), 8.00 (s, 1H), 8.07 (d, J=8.6 Hz, 2H), 8.63 (s, 1H).

Analogous to the condensation reaction described above and illustrated in the foregoing specific examples, the following further exemplary compounds of the invention can be prepared:

N-(4,4-dimethyl-6-)chromanyl 4-methoxycarbonyl benzaldimine;

N-(4,4-dimethyl-6-)chromanyl 4-carboxy benzaldimine;

N-(4,4-dimethyl-6-)chromanyl 4-ethoxycarbonyl benzaldimine;

N-(4,4-dimethyl-7-)chromanyl 4-methoxycarbonyl benzaldimine;

N-(4,4-dimethyl-7-)chromanyl 4-carboxy benzaldimine;

N-(4,4-dimethyl-7-)chromanyl 4-ethoxycarbonyl benzaldimine;

N-(2,2,4,4-tetramethyl-6-)chromanyl 4-methoxycarbonyl benzaldimine;

N-(2,2,4,4-tetramethyl-6-)chromanyl 4-carboxy benzaldimine;

N-(2,2,4,4-tetramethyl-7-)chromanyl methoxycarbonyl benzaldimine;

N-(2,2,4,4-tetramethyl-7-)chromanyl 4-carboxy benzaldimine;

N-(2,2,4,4-tetramethyl-7-)chromanyl 4-ethoxycarbonyl benzaldimine;

N-(4,4-dimethyl-6-)thiochromanyl 4-methoxycarbonyl benzaldimine;

N-(4,4-dimethyl-6-)thiochromanyl 4-carboxy benzaldimine;

N-(4,4-dimethyl-6-)thiochromanyl 4-ethoxycarbonyl benzaldimine;

N-(4,4-dimethyl-7-)thiochromanyl 4-methoxycarbonyl benzaldimine;

N-(4,4-dimethyl-7-)thiochromanyl 4-carboxy benzaldimine;

N-(4,4-dimethyl-7-)thiochromanyl 4-ethoxycarbonyl benzaldimine;

N-(2,2,4,4-tetramethyl-6-)thiochromanyl 4-methoxycarbonyl benzaldimine;

N-(2,2,4,4-tetramethyl-6-)thiochromanyl 4-ethoxycarbonyl benzaldimine;

N-(2,2,4,4-tetramethyl-6-)thiochromanyl 4-carboxy benzaldimine;

N-(2,2,4,4-tetramethyl-7-)thiochromanyl 4-methoxycarbonyl benzaldimine;

N-(2,2,4,4-tetramethyl-7-)thiochromanyl 4-carboxy benzaldimine;

N-(2,2,4,4-tetramethyl-7-)thiochromanyl 4-ethoxycarbonyl benzaldimine;

N-(4,4-dimethyl-1,2,3,4-tetrahydroquinolin-6-yl) 4-methoxycarbonyl benzaldimine;

N-(4,4-dimethyl-1,2,3,4-tetrahydroquinolin-6-yl) 4-carboxy benzaldimine;

N-(4,4-dimethyl-1,2,3,4-tetrahydroquinolin-6-yl)-ethoxycarbonyl benzaldimine;

N-(4,4-dimethyl-1,2,3,4-tetrahydroquinolin-7-yl)-methoxycarbonyl benzaldimine;

N-(4,4-dimethyl-1,2,3,4-tetrahydroquinolin-7-yl)-carboxy benzaldimine;

N-(4,4-dimethyl-1,2,3,4-tetrahydroquinolin-7-yl)-ethoxycarbonyl benzaldimine;

N-(2,2,4,4-tetramethyl-1,2,3,4-tetrahydroquinolin-yl)-4-methoxycarbonyl benzaldimine;

N-(2,2,4,4-tetramethyl-1,2,3,4-tetrahydroquinolin-yl)-4-ethoxycarbonyl benzaldimine;

N-(2,2,4,4-tetramethyl-1,2,3,4-tetrahydroquinolin-yl)-4-carboxy benzaldimine;

N-(2,2,4,4-tetramethyl-1,2,3,4-tetrahydroquinolin-yl)-4-methoxycarbonyl benzaldimine;

N-(2,2,4,4-tetramethyl-1,2,3,4-tetrahydroquinolin-yl)-4-carboxy benzaldimine;

N-(2,2,4,4-tetramethyl-1,2,3,4-tetrahydroquinolin-yl)-4-ethoxycarbonyl benzaldimine;

N-(5,6,7,8-tetrahydro-5,5,8,8-tetramethyl-2-naphthalenyl 3-methoxycarbonyl thiophene-5-carboxaldehyde imine;

N-(5,6,7,8-tetrahydro-5,5,8,8-tetramethyl-2-naphthalenyl 3-carboxy thiophene-5-carboxaldehyde imine;

N-(5,6,7,8-tetrahydro-5,5,8,8-tetramethyl-2-naphthalenyl 3-ethoxycarbonyl thiophene-5-carboxaldehyde imine;

N-(5,6,7,8-tetrahydro-5,5,8,8-tetramethyl-3-naphthalenyl 3-methoxycarbonyl thiophene-5-carboxaldehyde imine;

N-(5,6,7,8-tetrahydro-5,5,8,8-tetramethyl-3-naphthalenyl 3-carboxy thiophene-5-carboxaldehyde imine;

N-(5,6,7,8-tetrahydro-5,5,8,8-tetramethyl-3-naphthalenyl 3-ethoxycarbonyl thiophene-5-carboxaldehyde imine;

N-(5,6,7,8-tetrahydro-5,5,8,8-tetramethyl-2-naphthalenyl 3-methoxycarbonyl furan-5-carboxaldehyde imine;

N-(5,6,7,8-tetrahydro-5,5,8,8-tetramethyl-2-naphthalenyl 3-carboxy furan-5-carboxaldehyde imine;

N-(5,6,7,8-tetrahydro-5,5,8,8-tetramethyl-2-naphthalenyl 3-ethoxycarbonyl furan-5-carboxaldehyde imine;

N-(5,6,7,8-tetrahydro-5,5,8,8-tetramethyl-3-naphthalenyl 3-methoxycarbonyl furan-5-carboxaldehyde imine;

N-(5,6,7,8-tetrahydro-5,5,8,8-tetramethyl-3-naphthalenyl 3-carboxy furan-5-carboxaldehyde imine;

N-(5,6,7,8-tetrahydro-5,5,8,8-tetramethyl-3-naphthalenyl 3-ethoxycarbonyl furan-5-carboxaldehyde imine;

N-(4'-methoxycarbonyl)phenyl 5,6,7,8-tetrahydro-5,5,8,8-tetramethyl-naphthalene-2-carboxaldehyde imine;

N-(4'-carboxy)phenyl 5,6,7,8-tetrahydro-5,5,8,8-tetramethyl-naphthalene-2-carboxaldehyde imine;

N-(4'-methoxycarbonyl)phenyl 5,6,7,8-tetrahydro-5,5,8,8-tetramethyl-naphthalene-3-carboxaldehyde imine;

N-(4'-ethoxycarbonyl)phenyl 5,6,7,8-tetrahydro-5,5,8,8-tetramethyl-naphthalene-3-carboxaldehyde imine;

N-(4'-carboxy)phenyl 5,6,7,8-tetrahydro-5,5,8,8-tetramethyl-naphthalene-3-carboxaldehyde imine;

N-(4'-ethoxycarbonyl)phenyl 4,4-dimethyl-chroman-6-carboxaldehyde imine;

N-(4'-methoxycarbonyl)phenyl 4,4-dimethyl-chroman-carboxaldehyde imine;

N-(4'-carboxy)phenyl 4,4-dimethyl-chroman-6-carboxaldehyde imine;

N-(4'-ethoxycarbonyl)phenyl-4,4-dimethyl-chroman-7-carboxaldehyde imine;

N-(4'-methoxycarbonyl)phenyl 4,4-dimethyl-chroman-carboxaldehyde imine;

N-(4'-carboxy)phenyl 4,4-dimethyl-chroman-7-carboxaldehyde imine;

N-(4'-methoxycarbonyl)phenyl 2,2,4,4-tetramethyl-chroman-6-carboxaldehyde imine;

N-(4'-carboxy)phenyl-2,2,4,4-tetramethyl-chroman-6-carboxaldehyde imine;

N-(4'-ethoxycarbonyl)phenyl 2,2,4,4-tetramethyl-chroman-7-carboxaldehyde imine;

N-(4'-methoxycarbonyl)phenyl 2,2,4,4-tetramethyl-chroman-7-carboxaldehyde imine;

N-(4'-carboxy)phenyl-2,2,4,4-tetramethyl-chroman-7-carboxaldehyde imine;

N-(4'-ethoxycarbonyl)phenyl 4,4-dimethyl-thiochroman-6-carboxaldehyde imine;

N-(4'-methoxycarbonyl)phenyl 4,4-dimethyl-thiochroman-6-carboxaldehyde imine;

N-(4'-carboxy)phenyl 4,4-dimethyl-thiochroman-6-carboxaldehyde imine;

N-(4'-ethoxycarbonyl)phenyl 4,4-dimethyl-thiochroman-7-carboxaldehyde imine;

N-(4'-methoxycarbonyl)phenyl 4,4-dimethyl-thiochroman-7-carboxaldehyde imine;

N-(4'-carboxy)phenyl 4,4-dimethyl-thiochroman-7-carboxaldehyde imine;

N-(4'-ethoxycarbonyl)phenyl 2,2,4,4-tetramethyl-thiochroman-6-carboxaldehyde imine;

N-(4'-methoxycarbonyl)phenyl 2,2,4,4-tetramethyl-thiochroman-6-carboxaldehyde imine;

N-(4'-carboxy)phenyl 2,2,4,4-tetramethyl-thiochroman-6-carboxaldehyde imine;

N-(4'-ethoxycarbonyl)phenyl 2,2,4,4-tetramethyl-thiochroman-7-carboxaldehyde imine;

N-(4'-methoxycarbonyl)phenyl 2,2,4,4-tetramethyl-thiochroman-7-carboxaldehyde imine;

N-(4'-carboxy)phenyl 2,2,4,4-tetramethyl-thiochroman-7-carboxaldehyde imine;

N-(4'-ethoxycarbonyl)phenyl 4,4-dimethyl-1,2,3,4-tetrahydroquinoline-6-carboxaldehyde imine;

N-(4'-methoxycarbonyl)phenyl 4,4-dimethyl-1,2,3,4-tetrahydroquinoline-6-carboxaldehyde imine;

N-(4'-carboxy)phenyl 4,4-dimethyl-1,2,3,4-tetrahydroquinoline-6-carboxaldehyde imine;

N-(4'-ethoxycarbonyl)phenyl 4,4-dimethyl-1,2,3,4-tetrahydroquinoline-7-carboxaldehyde imine;

N-(4'-methoxycarbonyl)phenyl 4,4-dimethyl-1,2,3,4-tetrahydroquinoline-7-carboxaldehyde imine;

N-(4'-carboxy)phenyl 4,4-dimethyl-1,2,3,4-tetrahydroquinoline-7-carboxaldehyde imine;

N-(4'-ethoxycarbonyl)phenyl 2,2,4,4-tetramethyl-1,2,3,4-tetrahydroquinoline-6-carboxaldehyde imine;

N-(4'-methoxycarbonyl)phenyl 2,2,4,4-tetramethyl-1,2,3,4-tetrahydroquinoline-6-carboxaldehyde imine;

N-(4'-carboxy)phenyl 2,2,4,4,-tetramethyl-1,2,3,4-tetrahydroquinoline-6-carboxaldehyde imine;

N-(4'-ethoxycarbonyl)phenyl 2,2,4,4-tetramethyl-1,2,3,4-tetrahydroquinoline-7-carboxaldehyde imine;

N-(4'-methoxycarbonyl)phenyl 2,2,4,4-tetramethyl-1,2,3,4-tetrahydroquinoline-7-carboxaldehyde imine;

N-(4'-carboxy)phenyl 2,2,4,4-tetramethyl-1,2,3,4-tetrahydroquinoline-7-carboxaldehyde imine;

N-(4'-ethoxycarbonyl)-2-thienyl 5,6,7,8-tetrahydro-5,5,8,8-tetramethyl-naphthalene-2-carboxaldehyde imine;

N-(4'-methoxycarbonyl)-2-thienyl 5,6,7,8-tetrahydro-5,5,8,8-tetramethyl-naphthalene-2-carboxaldehyde imine;

N-(4'-carboxy)-2-thienyl 5,6,7,8-tetrahydro-5,5,8,8-tetramethyl-naphthalene-2-carboxaldehyde imine;

N-(5'-ethoxycarbonyl)-2-thienyl 5,6,7,8-tetrahydro-5,5,8, 8-tetramethyl-naphthalene-2-carboxaldehyde imine;

N-(5'-methoxycarbonyl)-2-thienyl 5,6,7,8-tetrahydro-5,5, 8,8-tetramethyl-naphthalene-2-carboxaldehyde imine;

N-(5'-carboxy)-2-thienyl 5,6,7,8-tetrahydro-5,5,8,8-tetramethyl-naphthalene-2-carboxaldehyde imine;

N-(4'-ethoxycarbonyl)-2-furyl 5,6,7,8-tetrahydro-5,5,8,8-tetramethyl-naphthalene-2-carboxaldehyde imine;

N-(4'-methoxycarbonyl)-2-furyl 5,6,7,8-tetrahydro-5,5,8, 8-tetramethyl-naphthalene-2-carboxaldehyde imine;

N-(4'-carboxy)-2-furyl 5,6,7,8-tetrahydro-5,5,8,8-tetramethyl-naphthalene-2-carboxaldehyde imine;

N-(5'-ethoxycarbonyl)-2-furyl 5,6,7,8-tetrahydro-5,5,8,8-tetramethyl-naphthalene-2-carboxaldehyde imine;

N-(5'-methoxycarbonyl)-2-furyl 5,6,7,8-tetrahydro-5,5,8, 8-tetramethyl-naphthalene-2-carboxaldehyde imine;

N-(5'-carboxy)-2-furyl 5,6,7,8-tetrahydro-5,5,8,8-tetramethyl-naphthalene-2-carboxaldehyde imine.

What is claimed is:

1. A compound of the formula

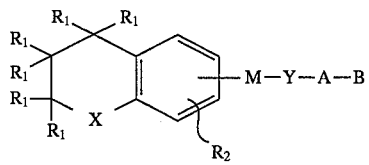

wherein the $R_1$ groups independently are hydrogen, lower alkyl of 1 to 6 carbons, or two geminal $R_1$ groups jointly represent an oxo (=O) or a thio (=S) group;

$R_2$ is hydrogen or lower alkyl of 1 to 6 carbons, or halogen;

M is —N=CR$_4$— where $R_4$ is hydrogen or lower alkyl of 1–6 carbons;

X is C(R$_1$)$_2$;

Y is a 1,4 phenyl group optionally substituted with an $R_3$ group which is lower alkyl of 1 to 6 carbons or halogen;

A is (CH$_2$)$_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is COOH or a pharmaceutically acceptable salt thereof, COOR$_8$, CONR$_9$R$_{10}$, —CH$_2$Oh, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, or CR$_7$OR$_{13}$O, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

2. A compound of claim 1 where A is (CH$_2$)$_n$ and n is 0 to 3.

3. A compound of claim 1 where B is COOH, or a pharmaceutically acceptable salt thereof, COOR$_8$ or CONR$_9$R$_{10}$.

4. A compound of the formula

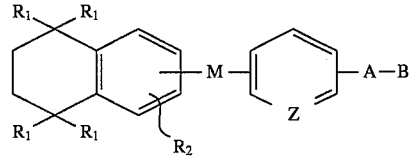

wherein the $R_1$ groups independently are hydrogen, lower alkyl of 1 to 6 carbons;

$R_2$ is hydrogen or lower alkyl of 1 to 6 carbons, or halogen;

M is —N=CR$_4$— where $R_4$ is hydrogen or lower alkyl of 1–6 carbons;

Z is CH;

A is (CH$_2$)$_n$ where n is 0–5, lower branched chain alkyl having 3–carbons, cycloalkyl having 3–6 carbons, alkenyl having 2–6 carbons and 1 or 2 double bonds, alkynyl having 2–6 carbons and 1 or 2 triple bonds;

B is COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO CH(OR$_{12}$)$_2$, CHOR$_{13}$O, —COR$_7$, CR$_7$(OR$_{12}$)$_2$, or CR$_7$OR$_{13}$O, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

5. A compound of claim 4 where the $R_1$ groups are CH$_3$, $R_2$ is H or CH$_3$, $R_4$ is H or CH$_3$, A is (CH$_2$)$_n$, n is O, and B is COOH, a pharmaceutically acceptable salt thereof, COOCH$_3$ or COOC$_2$H$_5$.

6. A compound of claim 5 where the —N=CR$_4$ group is attached to the 2 position of the tetrahydronaphthalene ring.

7. A compound of claim 6 which is selected from the group consisting of:

N-(5,6,7,8-tetrahydro-5,5,8,8-tetramethyl)-2-naphthalenyl 4-methoxycarbonyl benzaldimine, N-(5,6,7,8-tetrahydro-5,5,8,8-tetramethyl)-2-naphthalenyl 4-carboxy benzaldimine;

N-(5,6,7,8-tetrahydro-3,5,5,8,8-pentamethyl)-2-naphthalenyl 4-carboxy benzaldimine, N-(5,6,7,8-tetrahydro-5,5,8,8-tetramethyl)-2-naphthalenyl 4-ethoxycarbonyl benzaldimine, N-(5,6,7,8-tetrahydro-5,5,8,8-tetramethyl)-2-naphthalenyl 4-ethoxycarbonyl acetophenone imine, and N-(5,6,7,8-tetrahydro-3,5,5,8,8-pentamethyl)-2-naphthalenyl 4-ethoxycarbonyl benzaldimine.

* * * * *

UNITED STATES PATENT AND TRADEMARK OFFICE
CERTIFICATE OF CORRECTION

PATENT NO. : 5,498,755
DATED : March 12, 1996
INVENTOR(S) : Chandraratna et al.

It is certified that error appears in the above-indentified patent and that said Letters Patent is hereby corrected as shown below:

Title page, Abstract, item [57], line 11, "$CH_{2OR11}$" should be --$CH_2OR_{11}$--;

Column 10, line 35, "8-tetramethylnaphthalenecar-" should be --8-tetramethylnaphthalene-3 car- --;

Column 20, line 64, before "ethoxycarbonyl" please add -- 4- --;

Column 20, line 65, before "-meth-" please add -- -4 --;

Column 21, line 1, "-car" should be --4-car--;

Column 21, line 3, before "ethoxycarbony" please add -- 4- --;

Column 21, lines 5,7 and 9, all occurences of "-yl" should be --6-yl--;

Column 21, lines 11,13 and 15, all occurences of "-yl" should be --7-yl--;

Column 21, lines 17-41, before all "naphthalenyl" please add --)--;

Column 24, line 22, "3-carbons" should be --3-6 carbons--.

Signed and Sealed this

Twenty-fifth Day of February, 1997

Attest:

BRUCE LEHMAN

Attesting Officer

Commissioner of Patents and Trademarks